(12) United States Patent
Rao

(10) Patent No.: US 11,083,895 B2
(45) Date of Patent: Aug. 10, 2021

(54) SYSTEMS AND METHODS FOR AUGMENTING AND/OR RESTORING BRAIN AND NERVOUS SYSTEM FUNCTION AND INDUCING NEW NEURAL CONNECTIONS USING SELF-LEARNING ARTIFICIAL NETWORKS

(71) Applicant: University of Washington, Seattle, WA (US)

(72) Inventor: Rajesh Rao, Seattle, WA (US)

(73) Assignee: University of Washington, Seattle, WA (US)

(*) Notice: Subject to any disclaimer, the term of this patent is extended or adjusted under 35 U.S.C. 154(b) by 194 days.

(21) Appl. No.: 16/370,643

(22) Filed: Mar. 29, 2019

(65) Prior Publication Data

US 2019/0299008 A1    Oct. 3, 2019

Related U.S. Application Data

(60) Provisional application No. 62/650,174, filed on Mar. 29, 2018.

(51) Int. Cl.
*A61N 1/36* (2006.01)
*G06N 3/063* (2006.01)
(Continued)

(52) U.S. Cl.
CPC .......... *A61N 1/36139* (2013.01); *A61B 5/291* (2021.01); *A61B 5/6868* (2013.01);
(Continued)

(58) Field of Classification Search
CPC ............ A61N 1/36169; A61N 1/36014; A61N 1/36103; A61B 5/0478; A61B 5/6868; G06N 3/063
See application file for complete search history.

(56) References Cited

U.S. PATENT DOCUMENTS 7,010,351 B2   3/2006  Firlik et al.
7,209,787 B2   4/2007  DiLorenzo
(Continued)

FOREIGN PATENT DOCUMENTS

CN   101596338 A   12/2009
CN   106345056 A    1/2017
(Continued)

OTHER PUBLICATIONS

Adkins, D.L. et al., "Motor cortical stimulation promotes synaptic plasticity and behavioral improvements following sensorimotor cortex lesions," ScienceDirect, Experimental Neurology 212 (2008), pp. 14-28.
(Continued)

*Primary Examiner* — Lindsey G Wehrheim
(74) *Attorney, Agent, or Firm* — Perkins Coie LLP

(57) ABSTRACT

Systems and methods for restoring and/or augmenting neural function are disclosed herein. One such method includes receiving signals associated with a first region of the nervous system of the individual, and generating a stimulation pattern based on (a) the signals associated with the first region of the nervous system and (b) a first artificial network. The method can further include outputting the stimulation pattern to (a) a second region of the nervous system to induce a behavioral output from the individual and (b) a second artificial network configured to predict the behavioral output from the individual. The method can also include comparing the induced behavioral output to the predicted behavioral output to generate an error signal. Parameters of the first artificial network can be adjusted using the error signal and the second artificial network to optimize the stimulation patterns and other output signals to achieve restoration and/or augmentation goals.

18 Claims, 5 Drawing Sheets

(51) Int. Cl.
  *A61B 5/00* (2006.01)
  *A61B 5/291* (2021.01)
(52) U.S. Cl.
  CPC ..... *A61N 1/36014* (2013.01); *A61N 1/36103* (2013.01); *G06N 3/063* (2013.01)

(56) References Cited

U.S. PATENT DOCUMENTS

| | | | |
|---|---|---|---|
| 7,209,788 | B2 | 4/2007 | Nicolelis et al. |
| 7,460,911 | B2 | 12/2008 | Cosendai et al. |
| 8,401,634 | B2 | 3/2013 | Whitehurst et al. |
| 9,302,103 | B1 | 4/2016 | Nirenberg |
| 9,489,623 | B1 | 11/2016 | Sinyavskiy et al. |
| 2002/0087201 | A1 | 7/2002 | Firlik et al. |
| 2003/0093129 | A1 | 5/2003 | Nicolelis et al. |
| 2005/0267597 | A1 | 12/2005 | Flaherty et al. |
| 2007/0239211 | A1 | 10/2007 | Lorincz et al. |
| 2008/0045775 | A1 | 2/2008 | Lozano |
| 2009/0306491 | A1 | 12/2009 | Haggers |
| 2009/0306741 | A1 | 12/2009 | Hogle et al. |
| 2010/0003656 | A1 | 1/2010 | Rosellini et al. |
| 2013/0090706 | A1 | 4/2013 | Nudo et al. |
| 2014/0358192 | A1 | 12/2014 | Wheeler Moss et al. |
| 2015/0012111 | A1 | 1/2015 | Contreras-vidal et al. |
| 2016/0048753 | A1 | 2/2016 | Sussillo et al. |
| 2016/0129276 | A1 | 5/2016 | Fried et al. |
| 2017/0020448 | A1 | 1/2017 | Williams et al. |
| 2018/0078770 | A1* | 3/2018 | Rickert ............ A61N 1/36139 |
| 2019/0321639 | A1 | 10/2019 | Rao et al. |

FOREIGN PATENT DOCUMENTS

| | | |
|---|---|---|
| KR | 20150136704 A | 12/2015 |
| KR | 20180001408 U | 5/2018 |
| WO | 2014025765 A2 | 2/2014 |
| WO | 2016182947 A1 | 11/2016 |
| WO | 2017100649 A1 | 6/2017 |
| WO | 2017112679 A1 | 6/2017 |
| WO | 2018047164 A1 | 3/2018 |

OTHER PUBLICATIONS

Allart, E. et al., "Parietomotor connectivity in the contralesional hemisphere after stroke: A paired-pulse TMS study," Clinical Neurophysiology, 128 (2017), pp. 707-715.
Bell, C.J. et al., "Control of a humanoid robot by a noninvasive brain-computer interface in humans," Journal of Neural Engineering 5 (2008), pp. 214-220.
Berger, T.W. et al., "A cortical neural prosthesis for restoring and enhancing memory," Journal of Neural Engineering 8 (2011), 11 pages.
Brown, J. et al., "Motor Cortex Stimulation for the enhancement of recovery from stroke: A prospective, Multicenter safety study," Neurosurgery 58: 2006: 464-473.
Dethier, J. et al., "Design and validation of a real-time spiking neural-network decoder for brain-machine interfaces," Journal of Neural Engineering 10 (2013), 12 pages.
Donoghue, J. et al., "Assistive technology and robotic control using motor cortex ensemble-based neural interface systems in humans with tetraplegia," J. Physical 579.3 (2007), pp. 603-611.
Ezzyat, Y. et al., "Closed-loop stimulation of temporal cortex rescues functional networks and improves memory," Nature Communications (2018) 9:365, 8 pages.
Guggenmos, D. et al., "Restoration of function after brain damage using a neural prosthesis," PNAS, Dec. 24, 2013, vol. 110, No. 52, pp. 21177-21182.
Hamilton, L. et al., "Neural Signal Processing and Closed-loop Control Algorithm Design for an Implanted Neural Recording and Stimulation System," IEEE, 2015, 6 pages.
Houston, B. et al., "Classifier-Based closed-loop deep brain stimulation for essential tremor," IEEE 2017, 5 pages.
Jure, F. et al., "BCI-FES system for neuro-rehabilitation of stroke patients," Journal of Physics 705 (2016, 9 pages.
Levy, R. et al., "Epidural Electrical Stimulation for stroke rehabilitation: results of the prospective, multicenter, randomized, single-blinded Everest trial," Neurorehabilitation and Neural Repair, 2016, vol. 30(2), pp. 107-119.
Li, Z. et al., "FE-Induced Muscular Torque Prediction with Evoked EMG Synthesized by NARX-Type Recurrent Neural Network," IEEE 2012, 6 pages.
Lucas, T. et al., "Myo-cortical crossed feedback reorganizes primate motor cortex output," The Journal of Neuroscience, Mar. 20, 2013, 33(12, pp. 5261-5274.
Mestais, C. et al., "WIMAGINE: Wireless 64-channel ECoG recording implant for long term clinical applications," IEEE Transactions on Neural Systems and Rehabilitation Engineering, vol. 23, No. 1, Jan. 2015, 12 pages.
Miller, K. et al., "Reorganization of large-scale physiology in hand motor cortex following hemispheric stroke," Neurology 76, Mar. 8, 2011, 4 pages.
Mishra, J. et al., "Closed-Loop Rehabilitation of Age-Related Cognitive Disorders," Semin Neurol. Nov. 2014; 34(5), pp. 584-590.
Moritz, C. et al., "Direct control of paralysed muscles by cortical neurons," Nature, vol. 456, Dec. 4, 2008, 5 pages.
Mrachacz-Kersting, et al., "An Associative Brain-Computer-Interface for Acute Stroke Patients," The Scientific World Journal, vol. 2014, 11 pages.
Nishimura, Y. et al., "Spike-timing-dependent plasticity in primate corticospinal connections induced during free behavior," Neuron 80, Dec. 4, 2013, pp. 1301-1309.
Piangerelli, M. et al., "A fully integrated wireless system for intracranial direct cortical stimulation, real-time electrocorticography data transmission, and smart cage for wireless battery recharge," Frontiers in Neurology, Aug. 25, 2014, 5 pages.
Rao, R., "Brain-Computer Interfacing," Cambridge University Press, 2013, 15 pages.
Rao, R., "Method for augmenting the brain and nervous system with self-learning artificial networks for rewiring neural circuits and achieving desired functional outcomes," Feb. 26, 2018, 1 page.
Rao, R., Towards Neural Co-Processors for the Brain: Combining Decoding and Encoding in Brain-Computer Interfaces, Paul G. Allen School of Computer Science and Engineering, 14 pages.
Rebesco, J. et al., "Altering function in cortical networks by short-latency, paired stimulation," IEEE, 2010, 4 pages.
Rebesco, J. et al., "Rewiring neural interactions by microstimulation," Frontiers in Systems Neuroscience, Aug. 23, 2019, 15 pages.
Rouse, A.G. et al., "A chronic generalized bi-directional brain-machine interface," Journal of Neural Engineering 8 (2011), 20 pages.
Savic, A. et al., "Feasibility of a Hybrid Brain-Computer Interface for Advanced Functional Electrical Therapy," The Scientific World Journal, vol. 2014, 11 pages.
Seeman, S. et al., "Paired stimulation for spike-timing-dependent plasticity in primate sensorimotor cortex," The Journal of Neuroscience, Feb. 15, 2017, pp. 1935-1949.
Sun, F. et al., "The RNS System: responsive cortical stimulation for the treatment of refractory partial epilepsy," Expert Reviews, pp. 1745-2422.
Sussillo, D. et al., "Generating coherent patterns of activity from chaotic neural networks," Neuron 63, Aug. 27, 2009, pp. 544-557.
Vansteensel, M. et al., "Fully implanted brain-computer interface in a locked-in patient with ALS," The New England Journal of Medicine, 375, Nov. 24, 2016, 7 pages.
Wright, J. et al., "A review of control strategies in closed-loop neuroprosthetic systems," Frontiers in Neuroscience, Jul. 12, 2016, 13 pages.
Zanos, S. et al., "Phase-locked stimulation during cortical beta oscillations produces bidirectional synaptic plasticity in awake monkeys," Current Biology 28, Aug. 20, 2018, pp. 2515-2526.
International Search Report and Written Opinion in International Application No. PCT/US2017/044012, dated Oct. 3, 2017, 8 pages.

(56) References Cited

OTHER PUBLICATIONS

Jackson, A. et al., "Long-term motor cortex plasticity induced by an electronic neural implant," Nature, vol. 444, p. 56-60, Nov. 2, 2006.
U.S. Appl. No. 16/319,648 for Rao et al., filed Jan. 22, 2019.
Zanos, S. et al., "The Neurochip-2: An Autonomous Head-Fixed Computer for Recording and Stimulating in Freely Behaving Monkeys," IEEE Transactions on Neural Systems and Rehabilitation Engineering, vol. 19, No. 4, p. 427-435, Aug. 2011.

* cited by examiner

SYSTEMS AND METHODS FOR AUGMENTING AND/OR RESTORING BRAIN AND NERVOUS SYSTEM FUNCTION AND INDUCING NEW NEURAL CONNECTIONS USING SELF-LEARNING ARTIFICIAL NETWORKS

CROSS-REFERENCE TO RELATED APPLICATION(S)

The present application claims priority to U.S. Provisional Application No. 62/650,174, filed Mar. 29, 2018, and titled "METHOD FOR AUGMENTING THE BRAIN AND NERVOUS SYSTEM WITH SELF-LEARNING ARTIFICIAL NETWORKS," which is incorporated herein by reference in its entirety.

STATEMENT REGARDING FEDERALLY SPONSORED RESEARCH

This invention was made with government support under Grant No. EEC-1028725, awarded by the National Science Foundation. The government has certain rights in the invention.

TECHNICAL FIELD

The present technology relates generally to restoring and/or augmenting brain and nervous system function. In particular, some embodiments of the present technology include systems and methods for inducing neuroplasticity in the nervous system of a subject for rehabilitation/restoration of function or for enhancing the capabilities of the nervous system of an able-bodied individual.

BACKGROUND

The human brain is one of the world's most powerful autonomous computers, but nevertheless remains a fragile organ that can be difficult to train and repair, and that is limited by the sensory inputs and processing capacity provided by the human body. The parallel functions of and similarities between the brain and typical silicon computers have prompted considerable interest in the field of brain-computer interfaces. Brain-computer interfaces may be able to address some of the limitations of the human brain as well as bolster our understanding of an organ with many functions and operations that remain to be understood. More specifically, the computational capabilities of biological neural networks and silicon computers are complementary. For example, human brains commonly transfer information bidirectionally with computers through normal sensory and motor channels. However, transferring information through direct recording of neural activity and electrical stimulation of brain sites is much more challenging. Nevertheless, recent advances in interface technologies, computing systems, and our understanding of the human brain have sparked new investigations into the potential of brain-computer interfaces that directly record and/or stimulate the brain.

DETAILED DESCRIPTION

Figure 1:
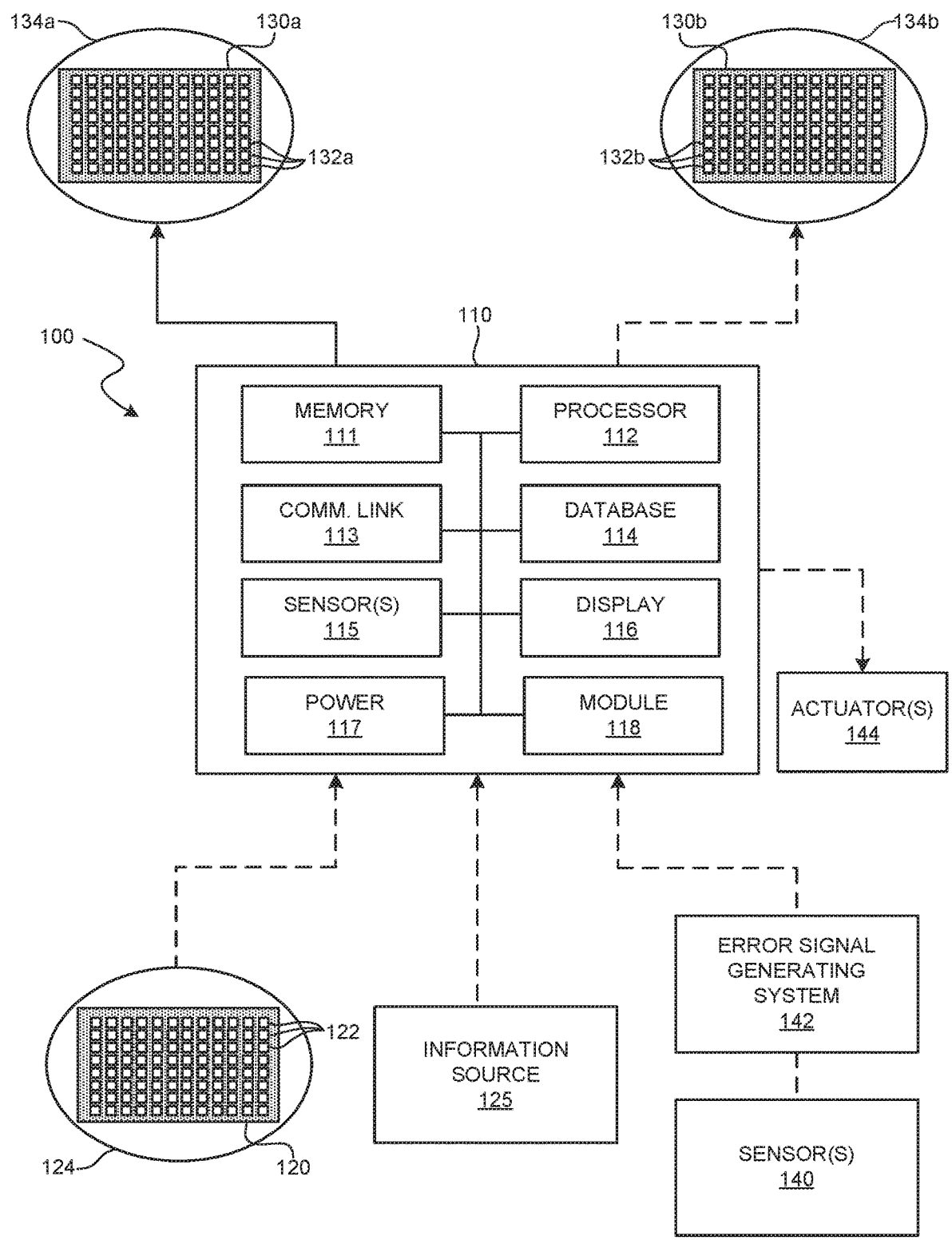
FIG. 1 is a partially schematic diagram of a system for augmenting and/or restoring neural function, and/or inducing new neural connections in a nervous system of a subject configured in accordance with embodiments of the present technology.

The present disclosure is directed generally toward systems and methods for restoring and/or enhancing neural function by inducing new neural connections in a nervous system (e.g., in the brain or spinal cord) of a subject. In several of the embodiments described below, for example, a system for restoring and/or enhancing neural function can include a stimulating component operably coupled to a computing device. The stimulating component is implanted within and/or worn externally by a subject proximate to a first region of their nervous system. The stimulating component can be configured to (a) receive a stimulation pattern and (b) stimulate the first region of the nervous system based on the received stimulation pattern to induce a behavioral output from the subject. The behavioral output can be, for example, a motor function, a sensory function, a memory function, and/or another function that is intended to be restored or enhanced.

The computing device can be configured to implement a first artificial network and a second artificial network. In some embodiments, the first and second artificial networks are self-learning deep recurrent neural networks. The first artificial network can be configured to (a) receive inputs associated with a second region of the nervous system, (b) generate the stimulation pattern based on the received inputs, and (c) output the stimulation pattern to the stimulating component. The second artificial network can be configured to (a) receive the stimulation pattern and (b) predict the behavioral output from the subject. The computing device can further generate an error signal based on the induced behavioral output and the predicted behavioral output and adjust parameters of the first artificial network based on the error signal.

In some embodiments, the inputs associated with the second region of the nervous system can comprise neural signals recorded in the second region. Thus, the system can function to map the recorded neural signals to output stimulation patterns to augment/restore neural function and/or induce new neural connections between the first and second regions of the nervous system. In other embodiments, stimulation patterns are separately applied to the second region of the nervous system in addition to the first region. The stimulation patterns applied to the second region can induce neural activity in the second region, and the system can operate to map this neural activity as well as activity from a third region to the output stimulation patterns applied to the first and second regions to augment/restore neural function and/or induce new neural connections between the first and second regions of the nervous system.

In one aspect of the present technology, the error signal can be iteratively propagated (e.g., backpropagated) through the first neural network to iteratively adjust and optimize parameters of the first neural network. The optimization can function to minimize error between an intended/desired behavioral output and the actual behavioral output induced by stimulation.

In another aspect of the present technology, the computing device (a "co-processor") is effectively arranged "in parallel" with a portion of the nervous system of the subject (e.g., the brain) and operates synergistically with the brain to jointly optimize a task or behavior. The systems and methods described herein can be used to augment the natural computational abilities of the brain and promote neural plasticity for the creation of new natural pathways between different areas of the brain, nervous system, or body organs. These new neural pathways can function to replace lost neural function (e.g., resulting from injury) or to augment existing neural function in the brain or other parts of the nervous system.

Certain details are set forth in the following description and in FIGS. 1-5 to provide a thorough understanding of various embodiments of the present technology. In other instances, well-known structures, materials, operations and/ or systems often associated with neural stimulation and recording (e.g., hardware and methods for stimulating the nervous system of a subject and/or recording neural signals from the nervous system such as electrical, optical, magnetic, chemical, and ultrasound-based recording and stimulation methods), artificial networks, etc., are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the invention.

Many of the details, dimensions, angles and other features shown in the Figures are merely illustrative of particular embodiments of the disclosure. Accordingly, other embodiments can have other details, dimensions, angles and features without departing from the spirit or scope of the present invention. In addition, those of ordinary skill in the art will appreciate that further embodiments of the invention can be practiced without several of the details described below.

In the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1.

The following discussion provides a general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, and/or a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s) or a sound wave) over a period of time, or may be provided on any analog or digital network (e.g., packet switched, circuit switched, or other scheme).

FIG. 1 is a partially schematic diagram of a system 100 for augmenting and/or restoring neural function, and/or inducing new neural connections in a nervous system of a subject (e.g., a human patient or able-bodied individual—not shown) configured in accordance with an embodiment of the present technology. The system 100 includes a processing subsystem 110 configured to be communicatively/operably coupled to (a) one or more stimulation modules 130 including a first stimulation module 130a and optionally a second stimulation module 130b, and (b) optionally to a sensor module 120 and/or an information source 125. In some embodiments, the system 100 can include one or more features that are generally similar to the features of the systems for augmenting and/or restoring neural function disclosed in U.S. patent application Ser. No. 16/319,648, titled "NEURAL CO-PROCESSOR FOR RESTORATION AND AUGMENTATION OF BRAIN FUNCTION AND ASSOCIATED SYSTEMS AND METHODS," and filed Jan. 22, 2019, which is incorporated herein by reference in its entirety. A simplified example of a suitable processing subsystem is described in "*The Neurochip*-2: *An Autonomous Head-Fixed Computer for Recording and Stimulating in Freely Behaving Monkeys*," by Stavros Zanos, Andrew G. Richardson, Larry Shupe, Frank P. Miles, and Eberhard E. Fetz, IEEE Transactions on Neural Systems And Rehabilitation Engineering, Vol. 19, No. 4, pg. 427-435, August 2011, which is also incorporated herein by reference in its entirety. An application of such a subsystem to induce neuroplasticity using a simple spike detection method is described in "*Long-term motor cortex plasticity induced by an electronic neural implant*," by Andrew Jackson, Jaideep Mavoori, and Eberhard E. Fetz, Nature, Vol. 444, pg. 56-60, Nov. 2, 2006, which is also incorporated herein by reference in its entirety.

The sensor module 120 can be any type of sensor such as, for example, a sensor configured to detect neural signals in the nervous system of the subject (e.g., for detecting neuroelectrical activity, neurochemical activity, etc.), an ultrasonic sensor, an infrared sensor, or another type of sensor. Accordingly, the sensor module 120 can be configured to detect signals that are external (e.g., visual, audio, infrared or ultrasonic signals from an environment around the subject) and/or internal (e.g., neural signals from the nervous system of the subject) relative to the subject. In some embodiments, the sensor module 120 is implanted in and/or worn externally proximate to a neural region of interest 124 (e.g., a first region) of the subject. The neural region of interest 124 can be, for example, a region of the subject's brain or another portion of the subject's nervous system. In some embodiments, the sensor module 120 can be a multichannel sensor that includes a plurality of individual sensor elements 122. Individual elements of the sensor elements 122 can be configured to detect one or more signals generated at different locations in and/or on the region of interest 124. For example, where the region of interest 124 is a region of the subject's brain, the sensor elements 122 can be configured to provide a spatial and/or spatiotemporal sampling of neural signals generated over the region of interest 124. More specifically, the sensor elements 122 can be configured to detect one or more of spikes, firing rates, local field potentials, optical or blood-oxygen level dependent (BOLD) activity, electroencephalogram (EEG) or electrocorticographic (ECoG) oscillatory features such as alpha waves, beta waves, gamma waves, etc., and the like. In some embodiments, the number of individual sensor elements 122 (e.g., measurement channels) in the sensor module 120 can be selected to correspond to a characteristic of the region of interest 124 (e.g., the physical structure of the region, the degrees of freedom in a detectable signal at the region, the numbers of neurons in the region, etc.).

In some embodiments, the information source 125 is provided instead of, or in addition to, the sensor module 120. The information source 125 can comprise any source of information such as the Internet, a data structure containing data, a source of user input, another nervous system, etc., for providing input to the processing subsystem 110.

The first stimulation module 130a is configured to be positioned at or proximate to a first stimulation region 134a of the subject, and the second stimulation module 130b is configured to be positioned at or proximate to a second stimulation region 134b of the subject. The stimulation modules 130a-b can be implanted in and/or worn externally by the subject. The stimulation regions 134 can be, for example, regions of the brain of the subject, other regions of the nervous system of the subject (e.g., the spinal cord or different nerves), regions of muscle, and/or regions of an organ of the subject. The stimulation modules 130a-b can include any invasive or non-invasive hardware for stimulating the stimulation regions 134. For example, the stimulation modules 130a-b can be configured to stimulate the stimulation regions 134 using one or more of: electrical activation, optical activation, magnetic activation, ultrasonic activation, and chemical activation. In some embodiments, the stimulation modules 130a-b are multi-channel modules that each include a plurality of individual stimulating elements 132 (identified individually as first stimulating elements 132a and second stimulating elements 132b). Each of the stimulating elements 132a-b can be configured to stimulate the corresponding stimulation regions 134 at a different location in and/or on the stimulation region. For example, the stimulation regions 134 can be regions in the subject's brain (e.g., the primary motor cortex of the brain, a region of the brain implicated in a certain neural function, etc.) and the stimulating elements 132a-b can be configured to provide spatially and/or spatiotemporally differing stimulation patterns in and/or on the stimulation regions 134. In some embodiments, the number of individual stimulating elements 132a-b (e.g., stimulation channels) in the stimulation modules 130a-b can be selected to correspond to a characteristic (e.g., the physical structure) of the stimulation regions 134.

In some embodiments, the system 100 can omit the information source 125 and/or the second stimulation module 130b. For example, the system 100 can utilize the sensor module 120 and the first stimulation module 130a for implementing an activity-dependent process for restoring and/or augmenting neural function, as described in greater detail below with reference to FIGS. 2 and 3. In other embodiments, the system 100 can include both of the first and second stimulation modules 130a-b and include or omit the sensor module 120, the information source 125, or both for implementing a paired-stimulation process for restoring and/or augmenting neural function, as described in greater detail below with reference to FIGS. 4 and 5. In some such embodiments, the second stimulation module 130b can be positioned at or proximate to the region of interest 124 in place of the sensor module 120.

The processing subsystem 110 comprises several components including memory 111 (e.g., one or more computer readable storage modules, components, devices, etc.) and one or more processors 112. The memory 111 can be configured to store information (e.g., signal data, subject information or profiles, environmental data, data collected from one or more sensors, media files, etc.) and/or executable instructions that can be executed by the one or more processors 112. The memory 111 can include, for example, instructions for processing multi-channel sensor data from the sensor module 120 and/or information from the information source 125 using an adaptive method such as a machine learning or artificial neural network model, for suppressing noise and other artifacts from signals received from the sensor module 120, for generating stimulation patterns for output to the stimulation modules 130 based on the adaptive methods below, for generating commands to one or more actuators 144 (e.g., via an external control module 118 of the processing subsystem 110), and/or for executing and adjusting an artificial neural network model or other adaptive method, as described in further detail below.

The processing subsystem 110 also includes a communication link 113 (e.g., a wired communication link and/or a wireless communication link (e.g., Bluetooth, Wi-Fi, infrared, and/or another wireless radio transmission network)) and a database 114 configured to store data (e.g., signal data acquired from a region of interest, equations, filters, etc.) used in the techniques for co-adapting with, augmenting and/or restoring neural function, and/or inducing new neural connections in the subject, as disclosed herein. One or more (e.g., first) sensors 115 can provide additional data for use in augmenting and/or restoring function, and/or inducing new neural connections in the subject. The sensors 115 can also provide other data pertinent to a condition and/or environment of the subject. For example, the sensors 115 may include one or more ECoG or other neural sensors, voltammetry sensors of neurochemicals, blood pressure monitors, galvanometers, accelerometers, thermometers, hygrometers, blood pressure sensors, altimeters, gyroscopes, magnetometers, proximity sensors, barometers, microphones, cameras, Global Positioning System (GPS) sensors, Near Field Communication (NFC) sensors, etc. The sensors 115 can also be configured to provide information about the system 100 itself, such as an operating condition (e.g., power level, noise level, etc.) of any or all of the components included therein. One or more displays 116 can provide video output and/or graphical representations of data obtained by the system 100. The one or more displays 116 and/or other components of the processing subsystem 110 can include one or more input devices (e.g., buttons, touchscreens, keyboards, mice, joysticks, number pads, etc.) for receiving user input. A power supply 117 (e.g., a power cable, one or more batteries, and/or one or more capacitors) can provide electrical power to components of the processing subsystem 110 and/or the system 100. In embodiments that include one or more batteries (e.g., where the system 100 is a portable system), the power supply 117 can be configured to recharge, for example, via a power cable, inductive charging, and/or another suitable recharging method. Furthermore, in some embodiments the processing subsystem 110 may include the module 118 having one or more additional components for, for example, interfacing with the actuators 144 and/or other external devices (e.g., robotic limbs, manipulators, prosthetics, mobile robots, drones, humanoid robots, etc.).

In some embodiments, the processing subsystem 110 can include one or more components partially or wholly incorporated into the sensor module 120, the information source 125, and/or the stimulation modules 130a-b. In other embodiments, however, the processing subsystem 110 may include components remote from the sensor module 120, the information source 125, and/or the stimulation modules 130, and connected thereto by a communication network (e.g., the Internet and/or another network or cloud computers). In some embodiments, for example, at least a portion of the processing subsystem 110 may reside on a mobile device (e.g., a mobile phone, a tablet, a personal digital assistant, etc.) and/or a computer (e.g., a desktop computer, a laptop, etc.) communicatively coupled to the sensor module 120, the information source 125, and/or the stimulation modules 130a-b. Moreover, the processing subsystem 110 can be configured to be worn by the subject (e.g., carried by their body) and/or implanted in their body (e.g., in or on a region of their nervous system).

In some embodiments, the system 100 can optionally include one or more additional (e.g., second) sensors 140 and/or an error signal generating system 142. The second sensors 140 can be communicatively coupled to the error signal generating system 142 and/or directly communicatively coupled to the processing subsystem 110. The second sensors 140 can be configured to detect, measure, and/or record a behavioral output by the subject resulting from (e.g., induced by) stimulation of one or both of the stimulation regions 134 by the stimulation modules 130a-b. The behavioral output may be internal (e.g., a neural activity pattern, a neurochemical response, an emotion or feeling, etc.) or external (e.g., a motor response) relative to the subject. The output may also be actions of the actuators 144. Accordingly, the second sensors 140 may be internal (e.g., implanted within) relative to the subject and/or external to the subject (e.g., externally affixed to the subject, to the actuators 144, and/or elsewhere in the external environment). The optional error signal generating system 142 can be communicatively coupled to the processing subsystem 110 and configured to generate an error signal and/or provide input about an error to the processing subsystem 110, as described in further detail below. The error signal generating system 142 can have some components generally similar to those of the system 100 (e.g., one or more processors, sensors, memory, etc.).

In some embodiments, the second sensors 140 and/or the error signal generating system 142 may be partially or wholly incorporated into the processing subsystem 110, the stimulation modules 130, the information source 125, and/or the sensor module 120, or omitted entirely. For example, the function of the second sensors 140 may be performed by the first sensors 115 of the processing subsystem 110, or the second sensors 140 can be omitted and any information about the measurable output from the subject can be determined by other means (by, e.g., an observing physician, researcher, user, etc.) and directly input via the processing subsystem 110 (via, e.g., the display 116 and/or other input devices).

Figure 2:
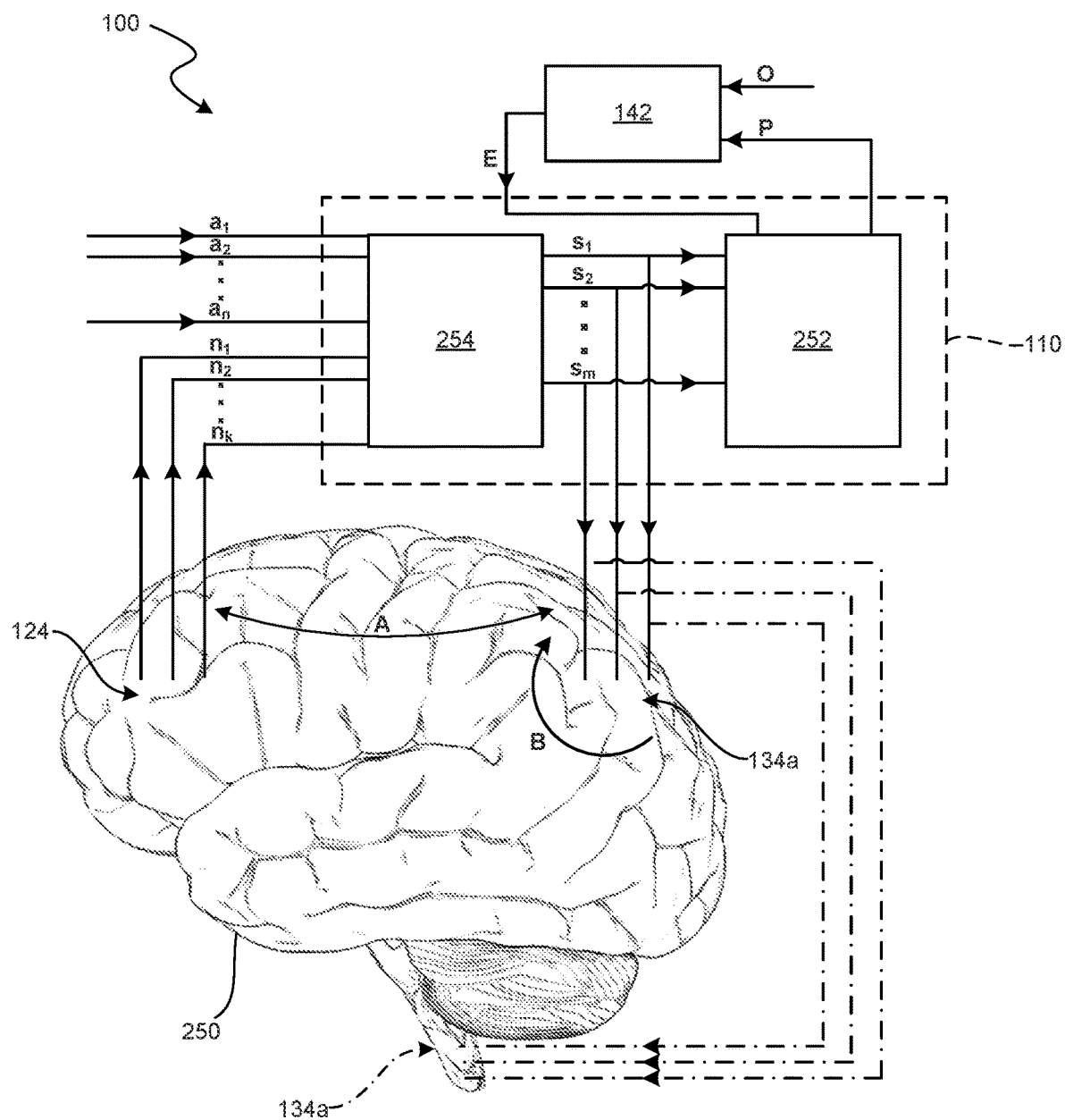
FIG. 2 is a schematic diagram of the system of FIG. 1 in an activity-dependent configuration in accordance with embodiments of the present technology.

FIG. 2 is a schematic view of the system 100 of FIG. 1 in an activity-dependent configuration for augmenting and/or restoring neural function in, for example, a brain 250 of an individual configured in accordance with embodiments of the present technology. In the illustrated embodiment, the processing subsystem 110 includes a first artificial neural network 252 (which can also be referred to herein as an emulator network) and a second artificial neural network 254 (which can also be referred to herein as a co-processor network). The neural networks 252, 254 can be multi-layered (e.g., deep) recurrent neural networks, self-learning artificial networks, or other suitable types of machine learning algorithms, artificial networks, etc., for mapping inputs to outputs. The memory 111 (FIG. 1) of the system 100 can store instructions executable by the one or more processors 112 (FIG. 1) for implementing the neural networks 252, 254.

In the illustrated embodiment, the system 100 dynamically detects and process neural activity at the region of interest 124. For example, the processing subsystem 110 is configured to receive and/or record a plurality of neural signals $n_1$-$n_k$ (e.g., via the sensor module 120 shown in FIG. 1) from the region of interest 124, which can be a region of the brain 250 of the subject. The neural signals $n_1$-$n_k$ are representative of neuroelectrical and/or neurochemical signals generated in the brain 250. In some embodiments, each of the neural signals $n_1$-$n_k$ is detected at and/or recorded from a different spatial location of the region of interest 124, and/or at one or more different times. In some embodiments, the processing subsystem 110 can further receive a plurality of augmentation signals $a_1$-$a_n$ from, for example, the sensor module 120 or information source 125 of FIG. 1. In some embodiments, the sensor module 120 includes an artificial sensor (e.g., a camera, a microphone, an infrared or ultrasonic sensor, etc.) such that the augmentation signals $a_1$-$a_n$ correspond to received artificial signals (e.g., visual signals, auditory signals, infrared signals, ultrasonic signals, etc.). In other embodiments, the augmentation $a_1$-$a_n$ can relate to any neural function to be augmented/restored and can be received from an information source such as the Internet.

As further shown in FIG. 2, the first neural network 252 is configured to receive the neural signals $n_1$-$n_k$ and optionally the augmentation signals $a_1$-$a_n$ and to generate and output a stimulation pattern comprising a plurality of stimulation signals $s_1$-$s_m$ each configured to stimulate a different portion of, for example, the first stimulation region 134a (via, e.g., the individual first stimulating elements 132a of the first stimulation module 130a shown in FIG. 1). In some embodiments, the neural network 252 can additionally generate control signals for controlling the external actuator(s)

144 (FIG. 1). In the illustrated embodiment, the first stimulation region 134a is a region of the brain 250 while, in other embodiments, the first stimulation region 134a can be a different region of the brain, and/or a different region in the nervous system (e.g., a region of the spinal cord as shown in phantom lines in FIG. 2), and/or a region of muscle or organ. In some embodiments, the first stimulation region 134a is a different region than the region of interest 124. For example, the first stimulation region 134a and the region of interest 124 can be regions of the nervous system that are separated by and/or functionally associated with an injured region of the nervous system. The injured region, for example, could be the result of a spinal cord injury, in which case the region of interest 124 can be a motor intention-forming region of the brain and the first stimulation region 134a can be a region of the spinal cord below the injury. Similarly, the injured region could be caused by a stroke, traumatic brain injury, or disease, and can partially or fully functionally disconnect the region of interest 124 from the first stimulation region 134a. The system 100 can therefore "straddle" an injured region of the nervous system and, as described in greater detail below, restore lost function and/or promote neural plasticity (e.g., by increasing neural connection strength) through the injured region and/or between the region of interest 124 and the first stimulation region 134a. In some embodiments (e.g., for sensory restoration), the system 100 may connect an external sensor (e.g., the sensor module 120) to an arbitrary brain region, or a brain region implicated in the sense to be restored.

In some embodiments, the stimulation signals $s_1$-$s_m$ are operable to stimulate the first stimulation region 134a simultaneously or nearly simultaneously, while in other embodiments the stimulation signals $s_1$-$s_m$ are operable to stimulate the first stimulation region 134a over a varying time period. In some embodiments, the (input) neural signals $n_1$-$n_k$ and/or the augmentation signals $a_1$-$a_n$ are directly mapped to the (output) stimulation signals $s_1$-$s_m$ such that there is a one-to-one correspondence between the signals (such that, e.g., n=m, k=m, n=k=m, and/or n+k=m.). However, the mapping of the neural signals $n_1$-$n_n$ and/or the augmentation signals $a_1$-$a_n$ to the stimulation signals $s_1$-$s_m$ can be any suitable mapping (e.g., n≠m, k≠m, k≠n≠m, etc.). For example, the number of output stimulation signals $s_1$-$s_m$ can depend on the specific anatomy of the first stimulation region 134a as well as the configuration of the first stimulation module 130a (e.g., the number of individual first stimulating elements 132a.) The stimulation signals $s_1$-$s_m$ can include electrical signals, optical signals, magnetic signals, ultrasonic signals, voltammetric signals, and/or other suitable signals.

Stimulation of the first stimulation region 134a with the stimulation signals $s_1$-$s_m$ produces a behavioral output that can be either external or internal to the subject. External outputs can include behavioral outputs such as motor responses of the subject (e.g., a physical movement of or speech by the subject), sensory responses of the subject (e.g., an ability to perceive a specific stimuli), subjective reports (e.g., a rating of an emotional state such as mood score for depression) etc. Internal outputs can include neural responses of the subject (e.g., a specific neuroelectrical or neurochemical activity pattern detected in the brain), feelings, thoughts, memories, or emotions of the subject, etc. In some embodiments, the output can be detected, recorded, and/or measured by one or more sensors (e.g., the second sensors 140) of the system 100. In other embodiments, the behavioral output is detected, recorded, and/or measured by the subject or another system, device, or person apart from the system 100 (e.g., a physician or researcher working with the subject). For example, the output can be a rating (e.g., a numerical rating) by the subject that corresponds to their satisfaction with a behavioral, emotional, or other output (e.g., result) of the stimulation. Regardless of the form of the behavioral output caused by the stimulation, the error signal generating system 142 of the system 100 is configured to receive a measured output signal O that corresponds to the behavioral output. For example, the measured output signal O can comprise measurements/data captured by the second sensors 140, subject input, physician or researcher input, etc. In general, the measured output signal O represents the result of applying the stimulation signals $s_1$-$s_m$ to the first stimulation region 134a.

The first neural network 252 can be trained to emulate the biological transformation between the stimulation of the first stimulation region 134a and the corresponding behavioral output from the subject resulting from (e.g., induced by) that stimulation. More specifically, the first neural network 252 can receive the stimulation signals $s_1$-$s_m$ from the second neural network 254 and map the received stimulation pattern to a predicted/desired output signal P. As described in greater detail below, the first neural network 252 can be deep recurrent neural network whose weights can be learned using backpropagation from a dataset consisting of a large number and/or variety of (a) stimulation patterns of the first stimulation region 134a and/or endogenous neural activity patterns in the first stimulation region 134a and (b) behavioral outputs induced by the application of the stimulation patterns to the first stimulation region 134a or associated with the endogenous neural activity patterns in the first stimulation region 134a.

In the illustrated embodiment, the error signal generating system 142 receives the measured output signal O and the predicted output signal P from the first neural network 252 and is configured to output an error signal E that corresponds to a difference between the predicted output signal P and the actual output signal O induced from the subject by the stimulation. The error signal E can be backpropagated through the first neural network 252 to optimize its predictions by minimizing errors. The error signal E can also be used to train the second neural network 254 by backpropagating the error signal E through the first neural network 252 but without changing its weights, and then backpropagating the error through the second neural network 254 to optimize its output stimulation patterns by changing its weights.

Figure 3:
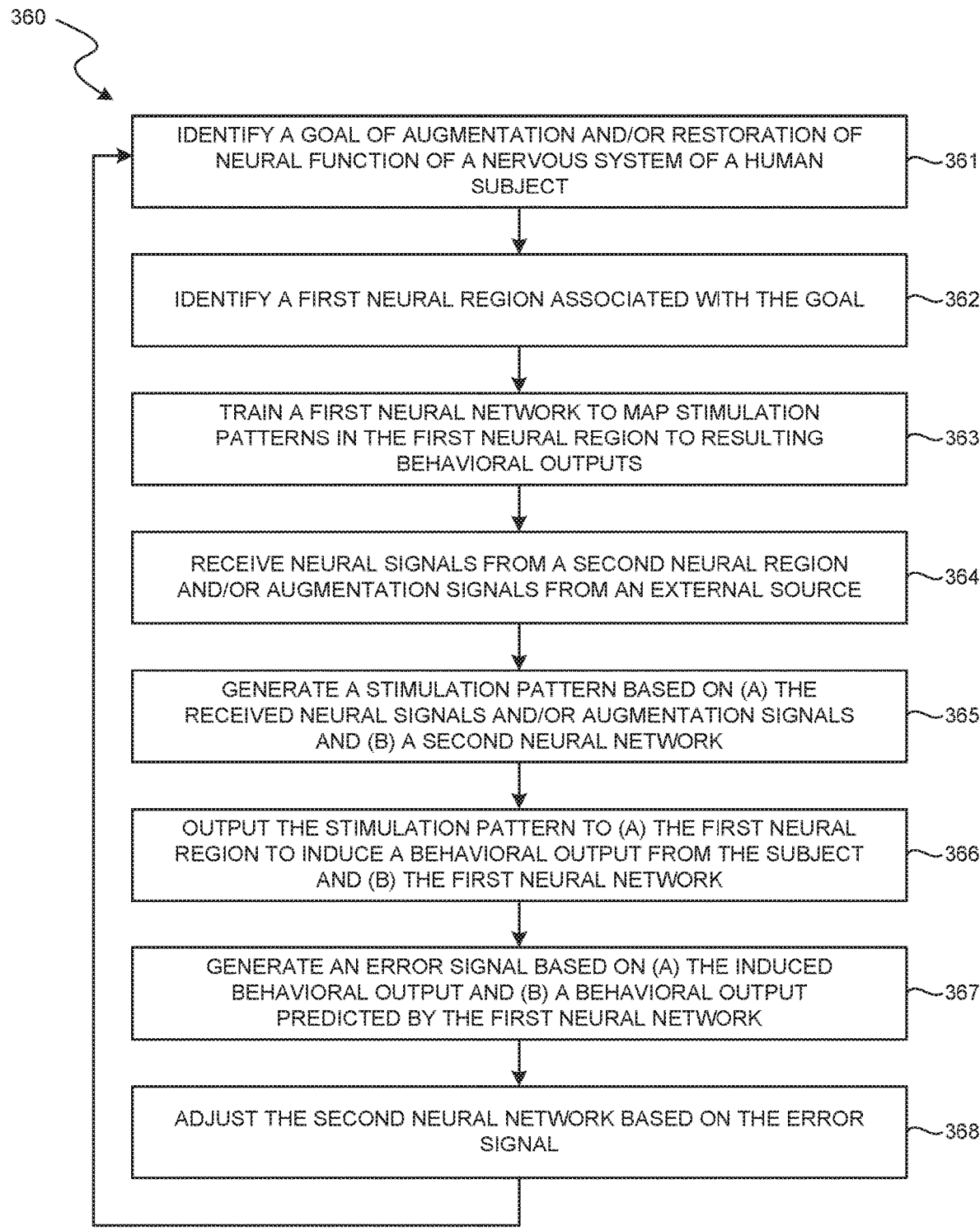
FIG. 3 is a flow diagram of a process or method for restoring or augmenting neural function using the activity-dependent configuration of the system in accordance with embodiments of the present technology.

FIG. 3 is a flow diagram of a process or method 360 for restoring lost neural function and/or augmenting neural function in a subject using the activity-dependent configuration of the system 100 in accordance with embodiments of the present technology. The process 360 can include instructions stored, for example, in the memory 111 of the system 100 (FIG. 1) that are executable by the one or more processors 112 (FIG. 1). In some embodiments, portions of the process 360 are performed by one or more hardware components (e.g., the sensor module 120 and/or the stimulation modules 130 of FIG. 1). In certain embodiments, portions of the process 360 are performed by a device external to the system 100 of FIG. 1. For the sake of illustration, some features of the process 360 will be described in the context of the embodiments shown in FIGS. 1 and 2.

Beginning at block 361, the process 360 includes identifying a goal of augmentation and/or restoration of neural function in a nervous system of a subject. For example, the goal can include restoring a set of movements (e.g., different types of hand grasps or movements) after a disabling injury.

As another example, the goal could include facilitating or restoring access to particular memories (e.g., those the subject can no longer access due to memory loss), or unlearning certain memories (e.g., traumatic memories that may contribute to post traumatic stress disorder (PTSD)). The goal could also include restoring or augmenting sensation and/or perception of the subject, augmenting or rehabilitating emotional function of the subject (e.g., via connecting or modifying connections in/between areas of the nervous system involved in emotion processing), augmenting or rehabilitating autonomic function (e.g., via connecting or modifying connections in/between areas of the nervous system involved in autonomic nervous system function), and/or augmenting the brain of the subject with knowledge, skills, information processing, information from artificial sensors, external actuation with robots and other devices, and/or learning capacities (e.g., via connecting the brain directly to an external information source).

At block 362, the process 360 includes identifying a first neural region associated with the goal. For example, when the goal is to restore a set of movements disabled by an injury, the first neural region could be an intact motor cortical area or spinal area below the injury. In the embodiment illustrated in FIG. 2, the first neural region is the first stimulation region 134a.

At block 363, the process 360 includes training the first neural network 252 to map stimulation patterns in the first stimulation region 134a to resulting behavioral outputs. In some embodiments, training the first neural network 252 can include building a dataset by stimulating different subsets of neurons in the first stimulation region 134a and recording the subsequently induced behavioral outputs (using, e.g., the second sensors 140). The first neural network 252 can then be trained—that is, the various parameters (e.g., weights) of the first neural network 252 can be adjusted—using backpropagation or another suitable technique based on the dataset. If the dataset is sufficiently large, the first neural network 252 can function as a surrogate for the biological networks that mediate the transformation between the stimulation patterns and the output behavior. In some embodiments, the dataset can further include endogenous neural activity in the first stimulation region 134a and the behavioral outputs associated with the endogenous neural activity.

In one special case of the present technology, the first neural network 252 may not be used if it is possible to discern a priori a set of distinct/discrete stimulation patterns that achieve the identified goal. In cases where such discrete stimulation patterns are known and the mapping between the stimulation patterns and the resulting behavioral outputs is more straightforward, the augmentation/restoration goal may be achieved with the use of the second neural network 254 alone. Such methods are described in detail in U.S. patent application Ser. No. 16/319,648, titled "NEURAL CO-PROCESSOR FOR RESTORATION AND AUGMENTATION OF BRAIN FUNCTION AND ASSOCIATED SYSTEMS AND METHODS," and filed Jan. 22, 2019, which is incorporated herein by reference in its entirety.

At block 364, the process 360 includes receiving the neural signals $n_1$-$n_k$ from a second neural region and/or the augmentation signals $a_1$-$a_n$ from an external source (e.g., the information source 125). In the embodiment illustrated in FIG. 2, the second neural region is the region of interest 124. In some embodiments, the neural signals $n_1$-$n_k$ are recorded while the subject performs a particular task. For example, if the identified goal (block 361) is to restore a motor function of the subject, the neural signals $n_1$-$n_k$ may be recorded while the subject performs or attempts to perform the specific motor function to be restored. If the identified goal is to restore or augment a sensory or cognitive function of the subject, the neural signals $n_1$-$n_k$ may be generated by the subject to access the function or information on the processing subsystem 110 or the information source 125.

At block 365, the process 360 includes generating a stimulation pattern based on (a) the received neural signals $n_1$-$n_k$ and/or the received augmentation signals $a_1$-$a_n$, and (b) the second neural network 254. More specifically, the second neural network 254 can receive as inputs the neural signals $n_1$-$n_k$ and/or the augmentation signals $a_1$-$a_n$ and map those signals to the output stimulation signals $s_1$-$s_m$. As described in greater detail below, the parameters (e.g., weights, amplitudes, time delays, etc.) of the second neural network 254 can be adapted to optimize the second neural network 254 and better map the input signals to an output stimulation pattern that achieves the desired behavioral output. In some embodiments, the second neural network 254 can generate control outputs for the actuator(s) 144 in addition to or instead of outputting stimulation patterns.

At block 366, the process 360 includes outputting the generated stimulation pattern to (a) the first stimulation region 134a and (b) the first neural network 252. Outputting the stimulation signals $s_1$-$s_m$ to the first stimulation region 134a induces a behavioral output from the nervous system of the subject. As described in detail above, the behavioral output could be a hand movement, the recall or erasure of a memory, speech, etc. The behavioral output is detected, recorded, and/or measured to generate the measured output signal O. The first neural network 252 is configured to receive as inputs the stimulation signals $s_1$-$s_m$ from the second neural network 254 and to output the predicted output signal P. In one aspect of the present technology, the first neural network 252 is trained before receiving the stimulation $s_1$-$s_m$ signals from the second neural network 254.

At block 367, the process 360 includes generating the error signal E based on (a) the behavioral output caused by applying the stimulation pattern to the first stimulation region 134a and (b) the predicted output signal P for this stimulation pattern generated by the first neural network 252. In the illustrated embodiment, the error signal generating system 142 receives and compares the measured output signal O and the predicted output signal P to generate the error signal E. As one example, where the behavioral output is an external motor response (e.g., a hand movement), the error signal E can be based at least in part on a difference (e.g., a physical distance) between the hand movement of the subject caused by application of the stimulation pattern (the output signal O) and a hand movement predicted by the first neural network 252 for the stimulation pattern (the predicted output signal P).

At block 368, the method includes adjusting the second neural network 254 based at least in part on the error signal E. For example, the error signal E can be can be used to adapt parameters of the second neural network 254 (e.g., to adjust one or more weights or values of one or more variables defining the second neural network 254) using an optimization method for minimizing error. In some embodiments, the optimization method can include backpropagating the error signal E through the first and second neural networks 252, 254—but only adapting the parameters of the second neural network 254 based thereon. That is, the process 360 need not include adapting the parameters of the first neural network 252 because the first neural network 252 has been pretrained (block 363). In one aspect of the present technology, because the first neural network 252 has been pretrained, the entire error signal E can be attributed to the operation of the second neural network 254. In some embodiments, the first neural network 252 and the second neural network 254 can be trained in an alternating manner: (i) train the first neural network 252, then (ii) switch to training the second neural network 254 while keeping the parameters of first neural network 252 fixed, then (iii) switch back to training the first neural network 252 while keeping the parameters of the second neural network 254 fixed, and so on. In a further embodiment, the neural networks 252, 254 may be trained simultaneously. In some embodiments, the variables of the second neural network 254 can be adjusted based on, for example, user input, data, information, and/or signals other than the error signal E, either continuously or at certain offline times. That is, in certain embodiments the process 360 is an adaptive process in which the adjustments to the second neural network 254 are based on signals or information different than the error signal E.

Lastly, the system returns to block 361 and the process 360 can be repeated. In this manner, the second neural network 254 can be optimized through iterative adjustments to minimize error between a resulting behavioral output and a desired behavioral output while, at the same time, optimizing the mapping from neural activity in the region of interest 124 and stimulation patterns in the first stimulation region 134a and, in the process, inducing (in some cases) new neural connections or modifying the strength of existing connections between the region of interest 124 and the first stimulation region 134a (represented by arrow A in FIG. 2). This process may increase plasticity through and/or around an injured region of the nervous system that is between the regions 124 and 134a to restore function that was previously lost as a result of an injury (e.g., a stroke or spinal cord injury). Thus, the process 360 causes the system 100 to "co-adapt" and jointly optimize with the nervous system of the subject to promote neuroplasticity, rewiring, and creation of new neural pathways between populations of neurons for restoration and rehabilitation.

Alternatively or additionally, the process 360 can cause the system 100 to co-adapt and jointly optimize task performance with the nervous system to (a) incorporate the system 100 (i.e., a neural co-processor) within the nervous system's computational processing pathways, and (b) promote neuroplasticity, rewiring, and creation of new neural pathways between populations of neurons, allowing the combined nervous system and computing system to learn a new skill or new sensation, and augment the brain's computational capacities. For example, in the embodiment of FIG. 2, new neural pathways can be induced within the brain 250 (e.g., within or between the region of interest 124, the first stimulation region 134a, and other regions directly or indirectly connected to these regions) as represented by the arrows A and B. Over time, dependence on the system 100 may be gradually reduced and the system 100 may be removed if sufficient function has been restored by the neuroplasticity induced by the use of system 100 over an extended period of time. In some embodiments, the system 100 may be configured as a permanent neural prosthesis.

In contrast to conventional brain-computer interfaces that use neural activity in the brain to control external devices, the present technology is directed to a bidirectional brain-computer interface having recurrent connections that allow activity-dependent stimulation of the brain, spinal cord, muscles and/or other organs, in addition to incorporating external sensory or other information into its information processing and allowing control of external actuators. Such a brain-computer interface can be made sufficiently small to be worn externally and/or implanted in a subject and operate autonomously during hours of free behavior.

Figure 4:
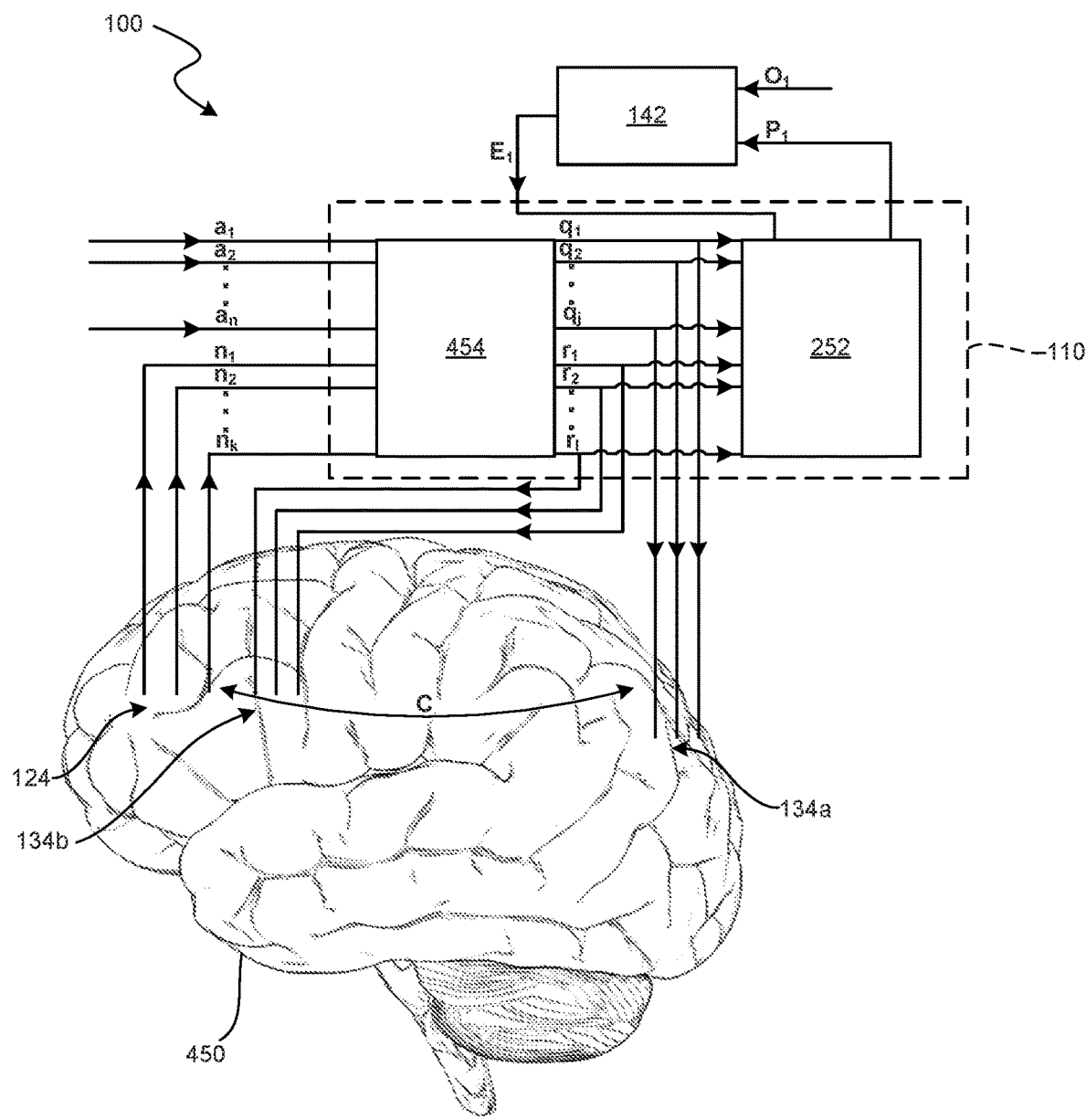
FIG. 4 is a schematic diagram of the system of FIG. 1 in a paired-stimulation configuration in accordance with embodiments of the present technology.

FIG. 4 is a schematic view of the system 100 of FIG. 1 in a paired-stimulation configuration for augmenting and/or restoring neural function in, for example, a brain 450 of an individual configured in accordance with embodiments of the present technology. In the illustrated embodiment, the processing subsystem 110 can include the first neural network 252 described in detail above and a second neural network 454 (which can also be referred to herein as a co-processor network). The second neural network 454 can be generally the same as the second neural network 254 described in detail above, but is configured to generate stimulation patterns in both of the stimulation regions 134 in addition to receiving the detected neural activity (i.e., neural signals $n_1$-$n_k$) in the region of interest 124 as input. The memory 111 (FIG. 1) of the system 100 can store instructions executable by the one or more processors 112 (FIG. 1) for implementing the neural networks 252, 454.

In the illustrated embodiment, the system is configured for paired stimulation—that is, for stimulating both the first stimulation region 134a and the second stimulation region 134b to augment and/or restore function, and/or induce new neural connection therebetween. More specifically, the system 100 is configured to output a second stimulation pattern comprising a plurality of second stimulation signals $r_1$-$r_l$ each configured to stimulate a different portion of the second stimulation region 134b (via, e.g., the individual second stimulating elements 132b of the second stimulation module 130b shown in FIG. 1). The second neural network 454 is configured to (a) receive as inputs the neural signals $n_1$-$n_k$ from the region of interest 124 and/or the external augmentation signals $a_1$-$a_n$, and (b) output both the second stimulation signals $r_1$-$r_l$ and a first stimulation pattern comprising a plurality of first stimulation signals $q_1$-$q_j$ each configured to stimulate a different portion of the first stimulation region 134a (via, e.g., the individual first stimulating elements 132a of the first stimulation module 130a shown in FIG. 1). In the illustrated embodiment, the stimulation regions 134 are different regions of the brain 450 that can, for example, bridge, straddle, or otherwise be functionally associated with an injured region of the brain 450. In other embodiments, the stimulation regions 134 can be different regions of the brain 450 or the nervous system of the subject. In some embodiments, the region of interest 124 may be the same as one or both of the stimulation regions 134. In other embodiments, the region of interest 124 may be different from both of the stimulation regions 134 and may correspond to one or more regions of the nervous system relevant to the goal of restoration and/or augmentation of neural function.

In some embodiments, the system 100 is configured to deliver the second stimulation signals $r_1$-$r_l$ to the second stimulation region 134b at one or more first times and then to deliver the first stimulation signals $q_1$-$q_j$ to the first stimulation region 134a at one or more second times, different than the first times. As described in greater detail below, delivering the first stimulation signals $q_1$-$q_j$ at appropriate times after the second stimulation signals $r_1$-$r_l$ can induce neuroplasticity between the stimulation regions 134 (e.g., as indicated by the arrow C). In some embodiments, the second stimulation signals $r_1$-$r_l$ are operable to stimulate the second stimulation region 134b simultaneously or nearly simultaneously, while in other embodiments the second stimulation signals $r_1$-$r_l$ are operable to stimulate the second stimulation region 134b over a varying time period. Likewise, the first stimulation signals $q_1$-$q_j$ can be delivered simultaneously, nearly simultaneously, or at varying times to the first stimulation region 134a. The number of the second stimulation signals $r_1$-$r_I$ and the first stimulation signals $q_1$-$q_J$ can be the same or different (1). For example, the number of the first stimulation signals $q_1$-$q_J$ and/or the number of the second stimulation signals $r_1$-$r_I$ can depend on the specific anatomy of the first stimulation region 134a and the second stimulation region 134b, respectively. The first stimulation signals $q_1$-$q_J$ and the second stimulation signals $r_1$-$r_I$ can include electrical signals, optical signals, magnetic signals, ultrasonic signals, voltammetric signals, and/or other suitable signals.

As described in detail above, stimulation of the stimulation regions 134 induces a behavioral output from the subject that can be either external or internal to the subject, such as a motor response, sensory response, memory response, etc. In some embodiments, the behavioral output can be detected, recorded, and/or measured by one or more sensors (e.g., the second sensors 140) of the system 100. In other embodiments, the output is detected, recorded, and/or measured by the subject or another system, device, or person apart from the system 100 (e.g., a physician or researcher working with the subject). Regardless of the form of the behavioral output caused by the stimulation of the stimulation regions 134, the error signal generating system 142 of the system 100 receives a measured output signal $O_1$ that corresponds to the behavioral output induced by the stimulation of the first stimulation region 134a with the first stimulation signals $q_1$-$q_J$ and stimulation of the second stimulation region 134b with the second stimulation signals $r_1$-$r_I$.

The first neural network 252 can be trained to emulate the biological transformation between stimulation of the stimulation regions 134 and the corresponding behavioral output resulting from that stimulation. More specifically, the first neural network 252 can receive the first stimulation signals $q_1$-$q_J$ and the second stimulation signals $r_1$-$r_I$ from the second neural network 454 and map these stimulation signals to a predicted/desired output signal $P_1$. In the illustrated embodiment, the error signal generating system 142 receives the measured output signal $O_1$ and the predicted output signal $P_1$ and is configured to output an error signal $E_1$ that corresponds to a difference between the predicted output of stimulation and the actual output induced from the subject by the stimulation. In some embodiments, the error signal $E_1$ can be backpropagated through the first neural network 252 and the second neural network 454 to optimize the second neural network 454 by changing one or more parameters (e.g., weights, time delays, etc.) of the second neural network 454, as described in detail above.

Figure 5:
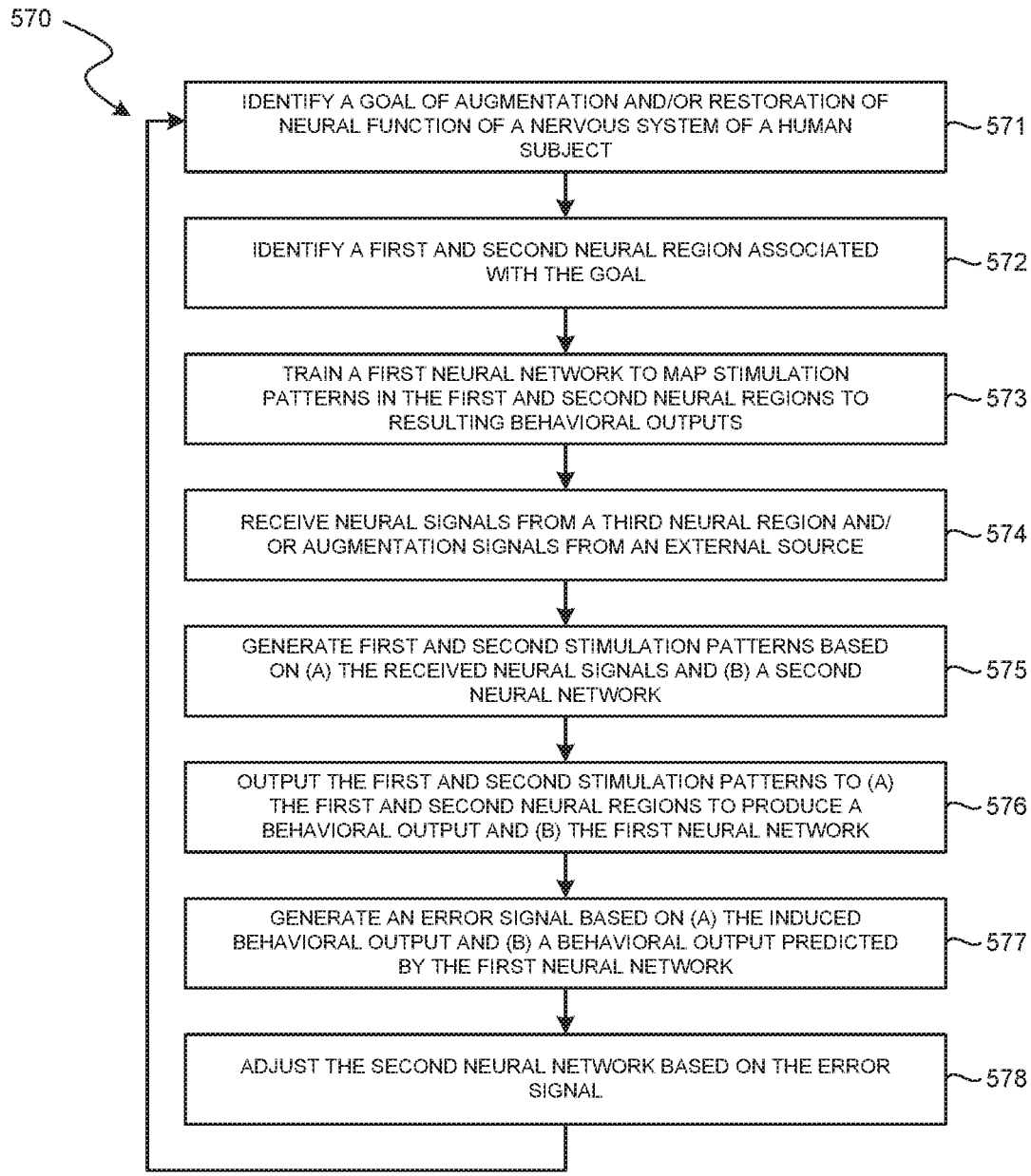
FIG. 5 is a flow diagram of a process or method for restoring or augmenting neural function using the paired-stimulation configuration of the system in accordance with embodiments of the present technology.

FIG. 5 is a flow diagram of a process 570 for restoring lost neural function and/or augmenting neural function in a subject using the paired-stimulation configuration of the system 100 in accordance with embodiments of the present technology. The process 570 can include instructions stored, for example, in the memory 111 of the system 100 (FIG. 1) that are executable by the one or more processors 112 (FIG. 1). In some embodiments, portions of the process 570 are performed by one or more hardware components (e.g., the sensor module 120 and/or stimulation modules 130 of FIG. 1). In certain embodiments, portions of the process 570 are performed by a device external to the system 100 of FIG. 1. For the sake of illustration, some features of the process 570 will be described in the context of the embodiments shown in FIGS. 1 and 4.

Some features of the process 570 can be generally similar to or the same as the features of the process 360 described in detail above with reference to FIG. 3. For example, blocks 571-573 of the process 570 can be the same as or generally similar to blocks 361-363 of the process 360. That is, the process 570 can include identifying a goal of augmentation and/or restoration of neural function in a nervous system of a subject, identifying neural regions associated with the goal (e.g., the stimulation regions 134), and training the first neural network 252 to map stimulation patterns in the stimulation regions 134 to resulting behavioral outputs.

At block 574, the process 570 includes receiving neural signals from a third neural region(s) known to be associated with the goal and/or external augmentation signals. For example, the process 570 can include receiving the neural signals $n_1$-$n_k$ from the region of interest 124 and/or the augmentation signals $a_1$-$a_n$ from an external source (e.g., the information source 125). In some embodiments, these inputs may be ignored, and pre-identified stimulation patterns may be used for the second stimulating region 134b. For example, if the goal is to restore motor function of the subject, the stimulation patterns for the second stimulating region 134b (e.g., a motor intention-forming brain region) can be based on neural activity patterns generated by the brain 450 when the subject thinks about performing the motor function. In other embodiments, the stimulation patterns can be based on neural activity patterns induced and identified by a stimulus, such as an auditory or visual stimulus.

At block 575 the process 570 includes generating first and second stimulation patterns (i.e., the first stimulation signals $q_1$-$q_J$ and the second stimulation signals $r_1$-$r_I$) based on the received neural signals and/or external augmentation signals and the second neural network 454. The first stimulation signals $q_1$-$q_J$ and the second stimulation signals $r_1$-$r_I$ are optimized by the network 454 to achieve the specific goal (e.g., behavioral output) of the augmenting and/or restoring of neural function. More specifically, as described in greater detail below, the parameters (e.g., weights, amplitudes, time delays, etc.) of the second neural network 454 can be adapted to optimize the second neural network 454 to better map the input signals to stimulation patterns that achieve the desired behavioral output.

At block 576, the process 570 includes outputting the generated first and second stimulation patterns to (a) the first and second stimulation regions 134a and 134b, respectively, to induce a behavioral output in the subject, and (b) to the first neural network 252.

Blocks 577 and 578 of the process 570 can be the same as or generally similar to the features of blocks 367 and 368, respectively, of the process 360 described in detail above with reference to FIG. 3. For example, the induced behavioral output (block 576) is detected, recorded, and/or measured to generate the measured output signal $O_1$, and the first neural network 252 processes the stimulation signals $q_1$-$q_J$ and $r_1$-$r_I$ to produce the predicted output signal $P_1$. The error signal generating system 142 or another component of the system 100 can receive and compare the measured output signal $O_1$ to the predicted output signal $P_1$ to generate the error signal $E_1$. The error signal $E_1$ can then be backpropagated through the first neural network 252 and the second neural network 454 to optimize the parameters of the second neural network 454 to minimize the error between the expected behavioral response and the actual behavioral response induced by stimulation of the first stimulation region 134a. Lastly, the system returns to block 571 and the process 570 can be repeated to optimize the second neural network 454 through iterative adjustments while, at the same time, restoring/augmenting neural function and/or inducing new neural connections between the stimulation regions 134 (represented by arrow C in FIG. 4).

In some cases, it may be possible to discern a priori a set of distinct/discrete stimulation patterns that achieve the identified goal. If such discrete stimulation patterns are known, the mapping between the stimulation patterns and the resulting behavioral outputs is more straightforward and, in some embodiments, can be achieved without the use of the first neural network 252. For example, referring to FIGS. 2-5 together, rather than training the first neural network 252 (blocks 363 and 573), the processes 360 and 570 can include identifying the distinct stimulation patterns that achieve the desired goal of stimulation. With these distinct stimulation patterns known and identified, the error signals E and $E_1$ can be more simply generated by directly comparing the output stimulation patterns generated by the second neural networks 254, 454 to the known stimulation patterns that trigger the desired behavioral output. Put differently, the first neural network 252 is not needed in such cases to compute a predicted behavioral output for generating an error signal. The error signals denote errors in stimulation patterns and can therefore be used to directly adjust the parameters of the second neural networks 254, 454, as described in detail above (e.g., via backpropagation).

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments (e.g., the disclosed system may include components for simultaneous augmentation and restoration of function in a nervous system of a subject).

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method for augmenting and/or restoring neural function in the brain and other parts of a nervous system of a subject, and/or inducing new neural connections in the nervous system, the method comprising:
receiving signals associated with a first region of the nervous system of the subject via a sensor implanted in and/or worn externally proximate to the first region of the nervous system, wherein the first region of the nervous system is a region in the brain or other region of the nervous system of the subject;
generating a stimulation pattern based on—
the signals associated with the first region of the nervous system, and
a first self-learning artificial network;
outputting the stimulation pattern to—
a second region of the nervous system to induce a behavioral output from the subject, wherein an injured region of the nervous system is between and/or functionally associated with the first and second regions of the nervous system; and
a second self-learning artificial network configured to predict the behavioral output from the subject;
generating an error signal based on the induced behavioral output and the predicted behavioral output;
adjusting parameters of the first artificial network using the error signal and the second artificial network;
artificially connecting the first and second regions with a self-learning artificial network and promoting neuroplasticity between the first and second regions to promote recovery and restoration of lost neural function of the subject.

2. The method of claim 1 wherein the stimulation pattern is a first stimulation pattern, and wherein a second stimulation pattern may be configured to be output to the first region of the nervous system.

3. The method of claim 1 wherein the first and second neural networks are deep recurrent neural networks.

4. The method of claim 1 wherein the method further includes adjusting parameters of the second artificial network by backpropagating the error signal through the second artificial network, and wherein adjusting the parameters of the first artificial network includes backpropagating the error signal through the first artificial network in the absence of the second artificial network.

5. The method of claim 1 wherein the method includes iteratively alternately adjusting parameters of the first and second artificial networks by—
adjusting the parameters of the first artificial network by backpropagating the error signal through the first and second artificial networks while keeping the parameters of the second artificial network fixed; and
adjusting the parameters of the second artificial network by backpropagating the error signal through the second artificial network while keeping the parameters of the first artificial network fixed.

6. The method of claim 1, further comprising training the second artificial network before outputting the stimulation pattern to the second artificial network, wherein training the second artificial network includes—
stimulating the second region with different stimulation patterns;
recording behavioral outputs induced from the subject and corresponding to the stimulation patterns; and
adjusting parameters of the second artificial network based on the different stimulation patterns and the corresponding behavioral outputs.

7. A method for augmenting and/or restoring neural function in the brain and other parts of a nervous system of a subject, and/or inducing new neural connections in the nervous system, the method comprising:
receiving signals associated with a first region of the nervous system of the subject;
generating a stimulation pattern based on— the signals associated with the first region of the nervous system, and
a first self-learning artificial network;
outputting the stimulation pattern to—
a second region of the nervous system to induce a behavioral output from the subject, and
a second self-learning artificial network configured to predict the behavioral output from the subject;
generating an error signal based on the induced behavioral output and the predicted behavioral output; and
adjusting parameters of the first artificial network using the error signal and the second artificial network, wherein adjusting the parameters of the first artificial network includes backpropagating the error signal through the second artificial network and then through the first artificial network, and
wherein the method does not include adjusting the parameters of the second artificial network based on the error signal.

8. The method of claim 4, further comprising:
receiving external signals via a sensor and/or information source that is external to the nervous system of the subject, wherein generating the stimulation pattern is further based on the external signals; and
generating commands for controlling one or more external actuators based on the signals associated with the first region of the nervous system, the external signals, and the first and second artificial networks.

9. A method for augmenting and/or restoring neural function and inducing new neural connections in a nervous system of a subject, the method comprising:
generating first and second stimulation patterns based on (a) neural activity in a region of interest, external signals, and/or prior knowledge of suitable stimulation patterns, and (b) an artificial network having one or more parameters;
outputting the first stimulation pattern to a first stimulation region of the nervous system and outputting the second stimulation pattern to a second stimulation region of the nervous system, wherein outputting the stimulation patterns induces a behavioral output from the subject;
generating an error signal based on the induced behavioral output; and
adjusting the parameters of the artificial network based on the error signal.

10. The method of claim 9 wherein the artificial network is a first artificial network, wherein the method further comprises outputting the first and second stimulation patterns to a second artificial network configured to predict the behavioral output from the subject, and wherein generating the error signal is based on the induced behavioral output and the predicted behavioral output.

11. The method of claim 10 wherein adjusting the parameters of the first artificial network includes backpropagating the error signal through the first and second artificial networks.

12. The method of claim 9 wherein outputting the first stimulation pattern includes stimulating the first stimulation region via a first stimulation module implanted in and/or worn externally proximate to the first stimulation region, and wherein outputting the second stimulation pattern includes stimulating the second stimulation region via a second stimulation module implanted in and/or worn externally proximate to the second stimulation region.

13. A system for augmenting and/or restoring neural function in the brain and other parts of the nervous system, and inducing new neural connections in a nervous system of a subject, the system comprising:
a stimulating component implanted within and/or worn externally by the subject proximate to a first region of the nervous system, wherein the stimulating component is configured to—
receive a stimulation pattern, and
stimulate the first region of the nervous system based on the stimulation pattern to induce a behavioral output from the subject; and
a computing device communicatively coupled to the stimulating component, the computing device having a memory containing computer-executable instructions and a processor for executing the computer-executable instructions contained in the memory, wherein the computer-executable instructions include instructions for—
implementing a first artificial network, wherein the first artificial network is configured to (a) receive inputs associated with a second region of the nervous system, (b) generate the stimulation pattern based on the inputs, and (c) output the stimulation pattern to the stimulating component;
implementing a second artificial network, wherein the second artificial network is configured to (a) receive the stimulation pattern and (b) predict the behavioral output from the subject;
generating an error signal based on the induced behavioral output and the predicted behavioral output; and
adjusting parameters of the first and/or second artificial networks based on the error signal.

14. The system of claim 13 wherein the inputs associated with the second region of the nervous system comprise neural signals.

15. The system of claim 14, further comprising a sensor configured to record the neural signals at the second region of the nervous system, wherein the sensor is implanted within and/or worn externally by the subject proximate to the second region.

16. The system of claim 13 wherein the stimulation pattern is a first stimulation pattern, and wherein the first artificial network is further configured to generate a second stimulation pattern configured to be output to the second region of the nervous system.

17. The system of claim 16 wherein the stimulating component is a first stimulating component, and further comprising a second stimulating component implanted within and/or worn externally by the subject proximate to the second region of the nervous system, wherein the second stimulating component is configured to (a) receive the second stimulation pattern and (b) stimulate the second region of the nervous system based on the second stimulation pattern to induce neural activity in the second region of the nervous system.

18. The system of claim 13 wherein the computing device is implanted in and/or worn by the subject.

* * * * *